United States Patent
Donnelly et al.

(10) Patent No.: US 11,134,711 B2
(45) Date of Patent: Oct. 5, 2021

(54) RICE HUSK FLOW AGENT

(71) Applicant: Firmenich SA, Geneva (CH)

(72) Inventors: Jeffrey W. Donnelly, Plainsboro, NJ (US); Anandaraman Subramaniam, Hightstown, NJ (US); Rutger Van Sleeuwen, Plainsboro, NJ (US); Jian Zhang, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 348 days.

(21) Appl. No.: 16/311,954

(22) PCT Filed: Jun. 30, 2017

(86) PCT No.: PCT/EP2017/066258
§ 371 (c)(1),
(2) Date: Dec. 20, 2018

(87) PCT Pub. No.: WO2018/002297
PCT Pub. Date: Jan. 4, 2018

(65) Prior Publication Data
US 2019/0200665 A1    Jul. 4, 2019

Related U.S. Application Data

(60) Provisional application No. 62/357,356, filed on Jun. 30, 2016.

(51) Int. Cl.
A23P 10/43    (2016.01)
A23L 7/10    (2016.01)
(Continued)

(52) U.S. Cl.
CPC .............. *A23P 10/43* (2016.08); *A23L 7/115* (2016.08); *A23L 27/70* (2016.08); *A23P 10/00* (2016.08);
(Continued)

(58) Field of Classification Search
CPC .......... A23P 10/00; A23P 10/43; A23L 7/115; A23L 27/70; A61K 8/9794;
(Continued)

(56) References Cited

U.S. PATENT DOCUMENTS 5,389,586 A * 2/1995 Rogers .................. C04B 35/803
501/87
6,362,143 B2 * 3/2002 Satoh .................... A61K 8/9794
510/130

(Continued)

FOREIGN PATENT DOCUMENTS

JP    H06172624 A    6/1994
JP    H119199 A    1/1999
(Continued)

OTHER PUBLICATIONS

Rosentrater et al. Flowability and Handling Characteristics of Bulk Solids and Powders. 2005.*
(Continued)

*Primary Examiner* — Anthony J Weier
(74) *Attorney, Agent, or Firm* — Armstrong Teasdale LLP

(57) ABSTRACT

Provided herein is a rice husk particles wherein at least 90%, by weight, of the total weight of the particles, has a diameter less than 25 μm.

10 Claims, 4 Drawing Sheets

(51) Int. Cl.
*A23L 27/00* (2016.01)
*C11B 9/00* (2006.01)
*A61Q 19/00* (2006.01)
*A61K 8/9794* (2017.01)
*A23P 10/00* (2016.01)
*A61Q 13/00* (2006.01)

(52) U.S. Cl.
CPC ............ *A61K 8/9794* (2017.08); *A61Q 19/00* (2013.01); *C11B 9/0003* (2013.01); *A23V 2002/00* (2013.01); *A61K 2800/10* (2013.01); *A61Q 13/00* (2013.01)

(58) Field of Classification Search
CPC .... A61K 2800/10; A61Q 19/00; A61Q 13/00; C11B 9/0003; A23V 2002/00
See application file for complete search history.

(56) References Cited

U.S. PATENT DOCUMENTS

| | | | |
|---|---|---|---|
| 2002/0017224 A1* | 2/2002 | Horton | ............... B03B 9/04 106/705 |
| 2010/0229465 A1* | 9/2010 | Ahm | ............... A01G 24/00 47/59 S |
| 2011/0217420 A1 | 9/2011 | Lerner | |
| 2015/0322243 A1* | 11/2015 | Jaerger | ............... C08K 3/013 524/47 |
| 2016/0032191 A1* | 2/2016 | Carlson | ............... C07G 1/00 428/319.3 |

FOREIGN PATENT DOCUMENTS

| | | |
|---|---|---|
| JP | 2001211843 A | 8/2001 |
| JP | 2002001154 A2 | 1/2002 |
| JP | 2009298653 A | 12/2009 |
| KR | 20040082612 A | 9/2004 |

OTHER PUBLICATIONS

International Search Report and Written Opinion, application PCT/EP2017/066258, dated Oct. 9, 2017.
Chunhui HE et al., Powder Technology, vol. 227, 2012, p. 51-60.
Zhou Hao et al., Fuel, vol. 164, 2016, p. 1-10.
WPI Abstract for RU 2438345 published 2012.

* cited by examiner

RICE HUSK FLOW AGENT

CROSS-REFERENCE

This application is a 371 filing of International Patent Application PCT/EP2017/066258 filed 30 Jun. 2017, which claims the benefit of U.S. Provisional Patent Application 62/357,356, filed 30 Jun. 2016, the contents of which is hereby incorporated by reference in its entirety.

FIELD

The technical field relates to spray dried formulation of flavors or fragrances.

BACKGROUND

Delivery systems for the controlled release of flavor or fragrance compounds and methods of making them have been reported. Flow agents are used to make spray dried particles easier process and handle. There is a market need of natural flow agent for improving powder flow properties. A rice by-product (rice husk such as Nu-Flow® from RIBUS, Inc.) is available on the market. However, Nu-Flow® has not been reported to function effectively as a flow agent for a poor-flowing spray dried powder. This invention describes a composition of rice hull particles with specified particle size and size distribution which significantly improves the functionality of rice hull as a natural flow agent. It is desirable to find flow agents that contain natural ingredients.

SUMMARY

Provided herein are Rice husk particles wherein at least 90%, by weight, of the total weight of the particles, has a diameter less than 25 μm.

Further provided herein are rice husk particles wherein at least 75%, by weight, of the total weight of the particles, has a diameter less than 15 μm.

Also provided herein are rice husk particles wherein at least 50%, by weight, of the total weight of the particles, has a diameter less than 10 μm.

Provided herein are rice husk particles wherein at least 50%, by weight, of the total weight of the particles, has a diameter less than 10 μm, and at least 75%, by weight, of the total weight of the particles, has a diameter less than 15 μm, and at least 90%, by weight, of the total weight of the particles has a diameter less than 25 μm.

Provided herein are rice husk particles wherein 70%, by weight, of the total weight of the particles, has a diameter less than 5 μm up to about 15 μm.

Further provided herein are rice husk particles wherein 90%, by weight, of the total weight of the particles, has a diameter less than 5 μm up to about 25 μm.

Also provided herein is a spray dried powder comprising a flavor or fragrance, a carrier and up to about 5% rice husk particles wherein the powder has flow-ability of about no more than 1,000 Pascal/kg.

Further provided herein is a method of making rice husk particles comprising milling rice husk such that 70% of the particles, by weight, of the total weight of the particles has a diameter less than 5 μm up to about 15 μm.

Further provided is a method of making rice husk particles comprising milling rice husk such that rice husk particles wherein 90%, by weight, of the total weight of the particles, has a diameter less than 5 μm up to about 25 μm.

DETAILED DESCRIPTION OF THE FIGURES

Figure 3:
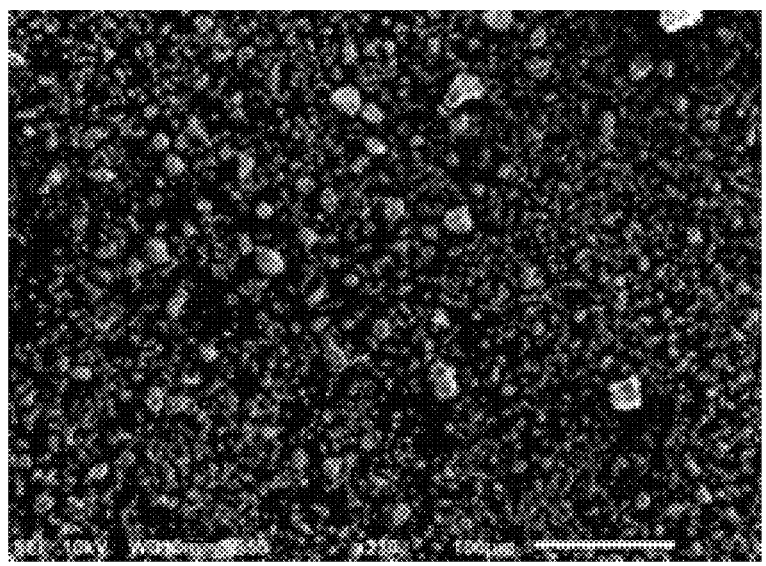
Figure 4:
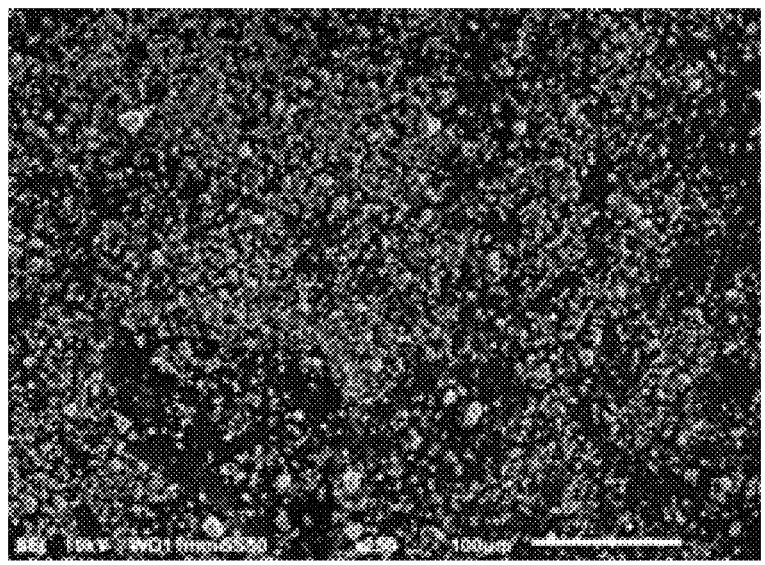
Figure 5:
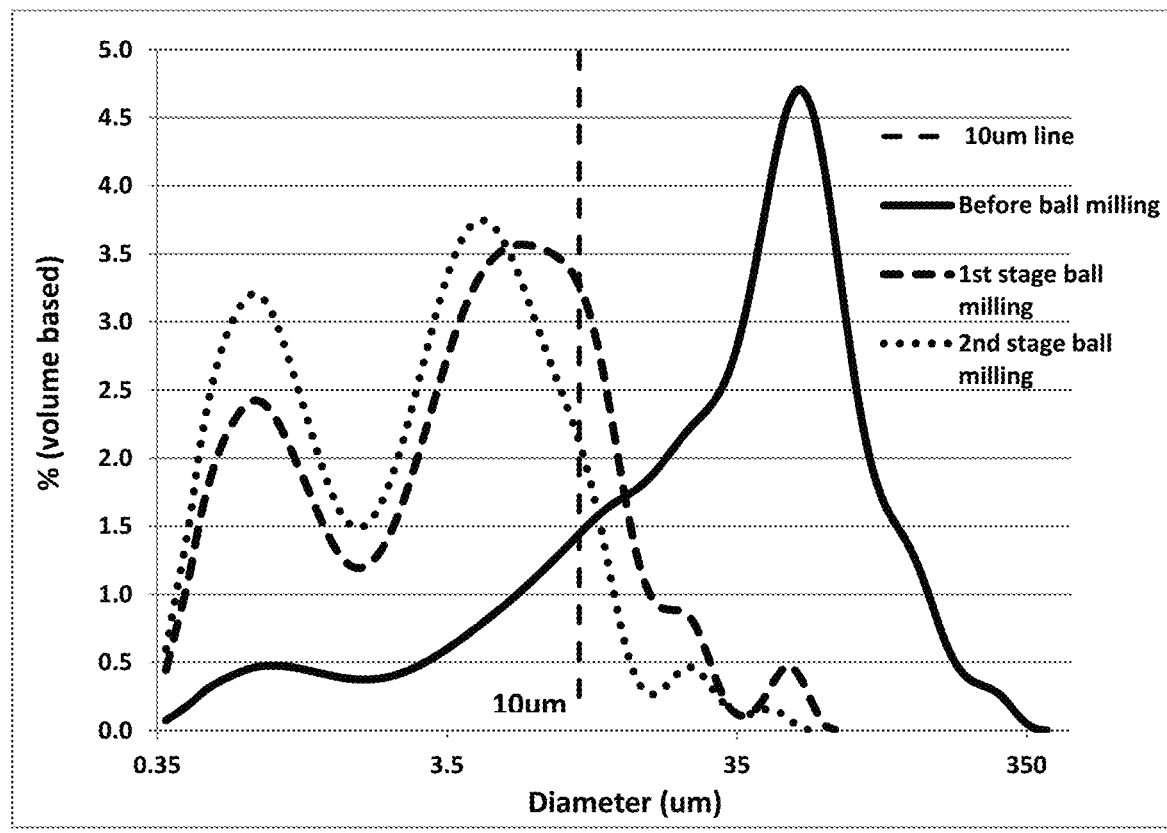

FIG. 3 shows an electron micrograph of rice husk after ball milling (first stage) for 72 hours FIG. 4 shows an electron micrograph of rice husk after ball milling (second stage) for 114 hours FIG. 5 shows the particle size distribution of rice husk before and after $1^{st}$ stage ball milling for 72 hours and $2^{nd}$ stage ball milling for 144 hours.

Figure 6:
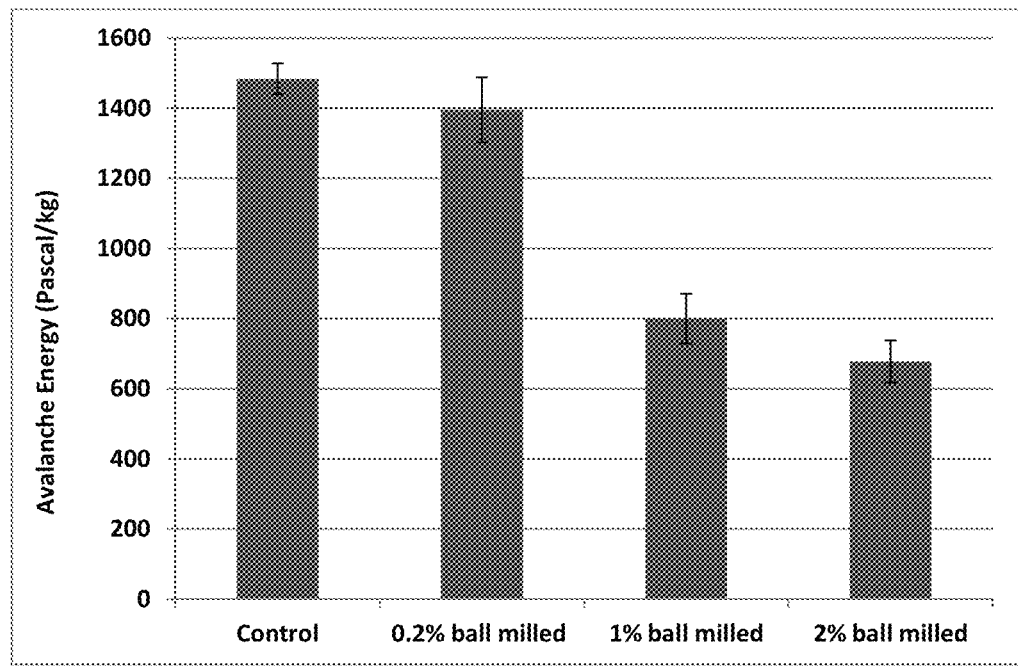

FIG. 6 shows the avalanche energy of orange spray dry powder with $1^{st}$ stage ball milled rice husk added as flow agent. The control is rice husk without ball milling.

Figure 7:
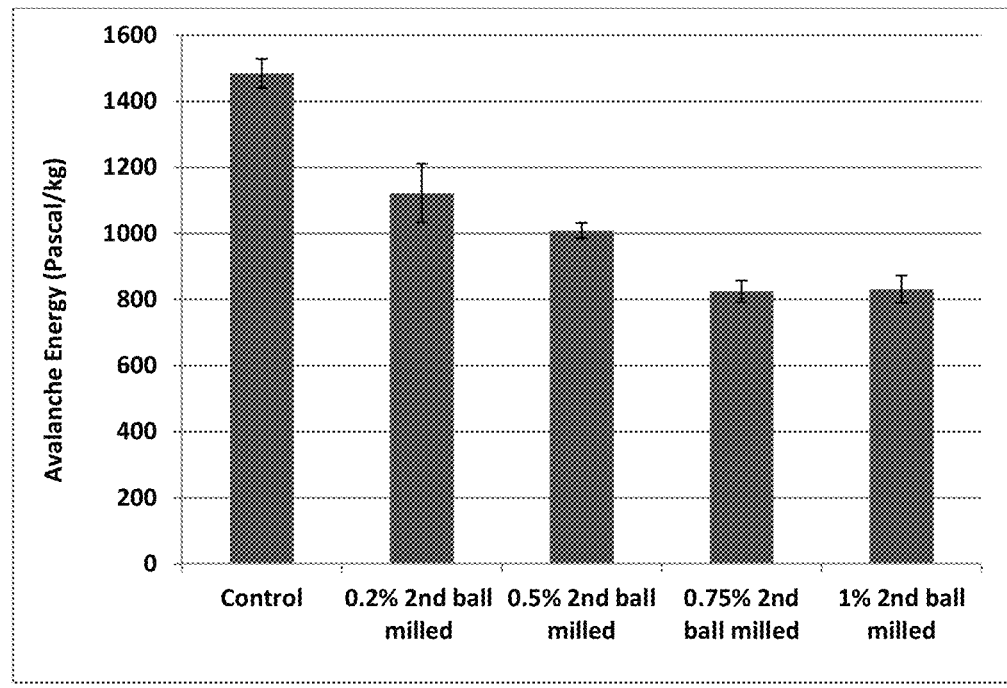

FIG. 7 shows the avalanche energy of orange spray dry powder with $2^{nd}$ stage ball milled Nu-Flow® added as flow agent. The control is Nu-Flow® without ball milling.

DETAILED DESCRIPTION

For the Summary, Description and Claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

In one embodiment, at least 50%, by weight, of the total weight of the particles, has a diameter less than 10 μm, and at least 75%, by weight, of the total weight of the particles, has a diameter less than 15 μm, and at least 90%, by weight, of the total weight of the particles has a diameter less than 25 μm.

In one embodiment, at least 70%, by weight, of the particles have a diameter less than 8 μm up to about 12 μm, particularly, about 10 μm.

In one embodiment, at least 90% by weight, of the particles have a diameter less than 8 μm to about 22 μm, particularly of about 20 μm.

In one embodiment, provided here is a method of making rice husk particles comprising milling rice husk such that at least 70% of the particles, by weight, of the total weight of the particles has a diameter less than about than 8 μm up to about 12 μm, more particularly at about 10 μm.

In one embodiment, provided here is a method of making rice husk particles comprising milling rice husk such that 90% of the particles, by weight, of the total weight of the particles has a diameter less than about than 8 μm up to about 22 μm, more particularly at about 20 μm.

In one embodiment the rice husk particles have at least 40%, by weight, of the total weight of the particles has a diameter less than 10 μm. More preferably, at least 50%, by weight, of the total weight of the particles has a diameter less than 10 μm. More preferably, at least 60%, by weight, of the total weight of the particles has a diameter less than 10 μm. More preferably, at least 70%, by weight, of the total weight of the particles has a diameter less than 10 μm. Even more preferably, at least 80%, by weight, of the total weight of the particles has a diameter less than 10 μm. Even more preferably, at least 90%, by weight, of the total weight of the particles has a diameter less than 10 μm.

In one embodiment, the milling process comprises ball milling.

In one embodiment, the milling process comprises jet milling.

In one embodiment, the particles are processes claimed herein are useful for making flavor or fragrance formulations.

In one embodiment provided herein comprises a flavor or fragrance, a carrier and up to about 5% rice husk particles wherein the powder has flowability of about no more than 1,000 Pascal/kg. By "flavor or flavoring composition", it is meant here a flavoring ingredient or a mixture of flavoring ingredients, solvents or adjuvants of current use for the preparation of a flavoring formulation, i.e. a particular mixture of ingredients which is intended to be added to an edible composition or chewable product to impart, improve or modify its organoleptic properties, in particular its flavor and/or taste. Flavoring ingredients are well known to a person skilled in the art and their nature does not warrant a detailed description here, which in any case would not be exhaustive, the skilled flavorist being able to select them on the basis of his general knowledge and according to the intended use or application and the organoleptic effect it is desired to achieve. Many of these flavoring ingredients are listed in reference texts such as in the book by S. Arctander, Perfume and Flavor Chemicals, 1969, Montclair, N.J., USA, or its more recent versions, or in other works of similar nature such as Fenaroli's Handbook of Flavor Ingredients, 1975, CRC Press or Synthetic Food Adjuncts, 1947, by M. B. Jacobs, van Nostrand Co., Inc. Solvents and adjuvants of current use for the preparation of a flavoring formulation are also well known in the art.

In a particular embodiment, the flavor is limonene flavor. In another embodiment, the flavor is a lemon flavor.

In another embodiment, the flavor is berry flavour.

In another embodiment, the flavor is peppermint flavor.

In another embodiment, the flavor is menthol flavor.

Flavors that are derived from or based on fruits where citric acid is the predominant, naturally-occurring acid include but are not limited to, for example, citrus fruits (e.g. lemon, lime), limonene, strawberry, orange, and pineapple. In one embodiment, the flavors are lemon, lime or orange juice extracted directly from the fruit. Further embodiments of the flavor comprise the juice or liquid extracted from oranges, lemons, grapefruits, key limes, citrons, clementines, mandarins, tangerines, and any other citrus fruit, or variation or hybrid thereof. In a particular embodiment, the flavor comprises a liquid extracted or distilled from oranges, lemons, grapefruits, key limes, citrons, clementines, mandarins, tangerines, any other citrus fruit or variation or hybrid thereof, pomegranates, kiwifruits, watermelons, apples, bananas, blueberries, melons, ginger, bell peppers, cucumbers, passion fruits, mangos, pears, tomatoes, and strawberries.

In a particular embodiment, the flavor comprises a composition that comprises limonene, in a particular embodiment, the composition is a citrus that further comprises limonene.

In another particular embodiment, the flavor comprises a flavor selected from the group comprising strawberry, orange, lime, tropical, berry mix, and pineapple.

The phrase flavor includes not only flavors that impart or modify the smell of foods but include taste imparting or modifying ingredients. The latter do not necessarily have a taste or smell themselves but are capable of modifying the taste that other ingredients provides, for instance, salt enhancing ingredients, sweetness enhancing ingredients, umami enhancing ingredients, bitterness blocking ingredients and so on.

In a further embodiment, suitable sweetening components may be included in the particles described herein. In a particular embodiment, a sweetening component is selected from the group consisting of sugar (e.g., but not limited to sucrose), a stevia component (such as but not limited to stevioside or rebaudioside A), sodium cyclamate, aspartame, sucralose, sodium saccharine, and Acesulfam K or mixtures thereof.

The dry particles provided herein may be suitable for conveying flavors to beverages, fluid dairy products, condiments, baked goods, frostings, bakery fillings, candy, chewing gum and other food products.

Beverages include, without limitation, carbonated soft drinks, including cola, lemon-lime, root beer, heavy citrus ("dew type"), fruit flavored and cream sodas; powdered soft drinks, as well as liquid concentrates such as fountain syrups and cordials; coffee and coffee-based drinks, coffee substitutes and cereal-based beverages; teas, including dry mix products as well as ready-to-drink teas (herbal and tealeaf based); fruit and vegetable juices and juice flavored beverages as well as juice drinks, nectars, concentrates, punches and "ades"; sweetened and flavored waters, both carbonated and still; sport/energy/health drinks; alcoholic beverages plus alcohol-free and other low-alcohol products including beer and malt beverages, cider, and wines (still, sparkling, fortified wines and wine coolers); other beverages processed with heating (infusions, pasteurization, ultra high temperature, ohmic heating or commercial aseptic sterilization) and hot-filled packaging; and cold-filled products made through filtration or other preservation techniques.

Fluid dairy products include, without limitation, non-frozen, partially frozen and frozen fluid dairy products such as, for example, milks, ice creams, sorbets and yogurts.

Condiments include, without limitation, ketchup, mayonnaise, salad dressing, Worcestershire sauce, fruit-flavored sauce, chocolate sauce, tomato sauce, chili sauce, and mustard.

Baked goods include, without limitation, cakes, cookies, pastries, breads, donuts and the like.

Bakery fillings include, without limitation, low or neutral pH fillings, high, medium or low solids fillings, fruit or milk based (pudding type or mousse type) fillings, hot or cold make-up fillings and nonfat to full-fat fillings.

In one embodiment, the encapsulated flavors provide an initial burst of flavor followed by a sustained release of the flavors.

In another aspect, a plasmolysed micro-organism cake and glass particles encapsulating the cake contain a higher load of flavor or fragrance over what is typically achieved for example through typical extrusion processes.

Particular fragrances that may be used herein are selected from the group consisting of 1-Pentyl-2-propenyl acetate, Hexylcinnamic aldehyde, 8,12-epoxy-13,14,15,16-tetranor-labdane, Tricyclo[5.2.1.0(2,6)]dec-3,4-en-1-yl acetate, Coumarine, 2-Pentyl-1-cyclopentanol, Cyclamen aldehyde, α-Damascone, Dihydromyrcenol, pentadecenolide, methyl ionone, Lilial®, Linalol, cis-4-(1,1-dimethyl)-1-cyclohexyl acetate, 3-methyl-(4,5)-cyclopentadecen-1-one, Tetrahydro-2-isobutyl-4-methyl-4(2H)-pyranol, γ-methyl-benzene pentanol, Hexyl salicylate, and Vertofix Coeur.

The following Examples are illustrative only and are not meant to limit the scope of the claims, the summary or any invention presented herein.

EXAMPLES

Introduction

Nu-Flow® rice husk made by RIBUS Inc. was evaluated as flow agent. The composition of Nu-Flow® is described in Table 1. The mineral content is about 16-22%. A Firmenich spray dried powder was used as an example (Control) of a poor flowing powder.

TABLE 1

Product composition of Nu-Flow ® rice husk

| Components | % by weight |
|---|---|
| Protein | 1-3 |
| Fat | 0-2 |
| Moisture | <4 |
| Carbohydrate | 60-76 |
| Ash (mineral) | 16-22 |

In the below experiments, the dynamic flowability of spray dried powders was evaluated using a Revolution Powder Analyzer (Mercury Scientific Inc., Newtown). The flowability of the powder was measured directly using the avalanche energy. The powder analyzer was set at rotation rate of 0.6 RPM, imaging rate of 30 frames per second, and total of 128 avalanches.

Particle size distribution was determined by Beckman Coulter LS 13 320 equipped with a powder module.

Example 1

Figure 1:
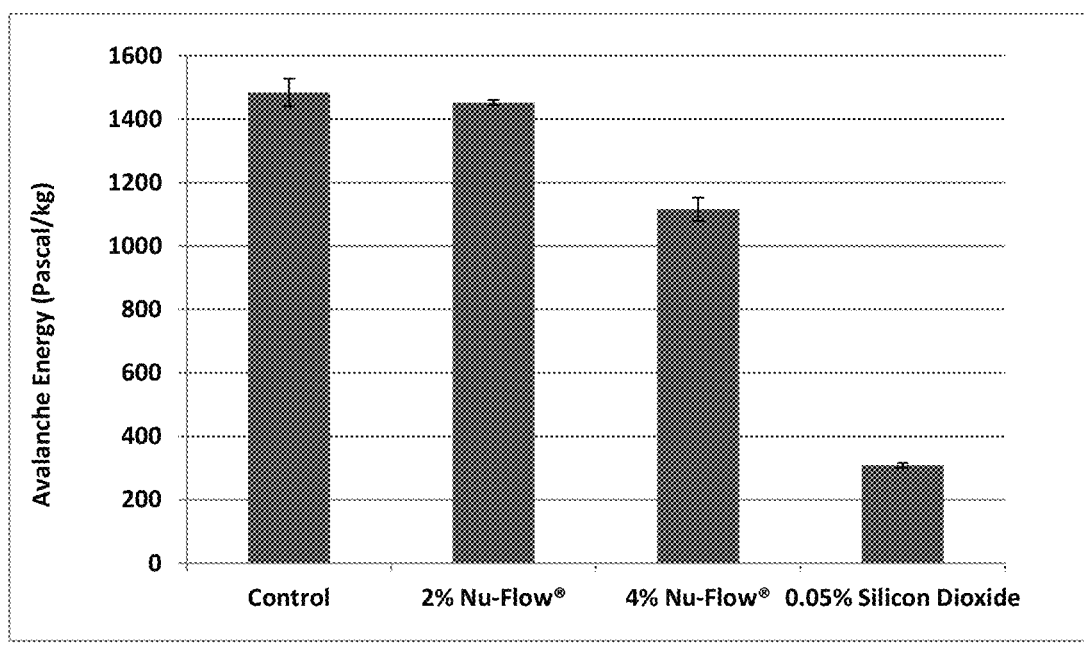
FIG. 1 shows the Avalanche energy of orange spray dry powder with rice husk or silicon dioxide added as flow agent. The control is without flow agent.

Silicon dioxide or rice husk was added to the Firmenich control powder ("Control") and mixed. The resultant powder mixture was blended manually (the powder was shaken in a small bag) until uniformly mixed. A sample was taken for analysis of flow properties. FIG. 1 provides a summary of the flow characteristics of the powders. The control had an avalanche energy of over 1400 Pascal/kg indicating poor flowability. When 0.05% silicon dioxide was added to the control powder, the avalanche energy decreased to about 300 Pascal/kg indicating that silicon dioxide is an effective flow agent. However, when Nu-Flow was added to the control powder (up to 4% by weight), the avalanche energy was 1100 Pascal/kg (4% of addition) indicating that rice husk as is does not function effectively as a flow agent.

Figure 2:
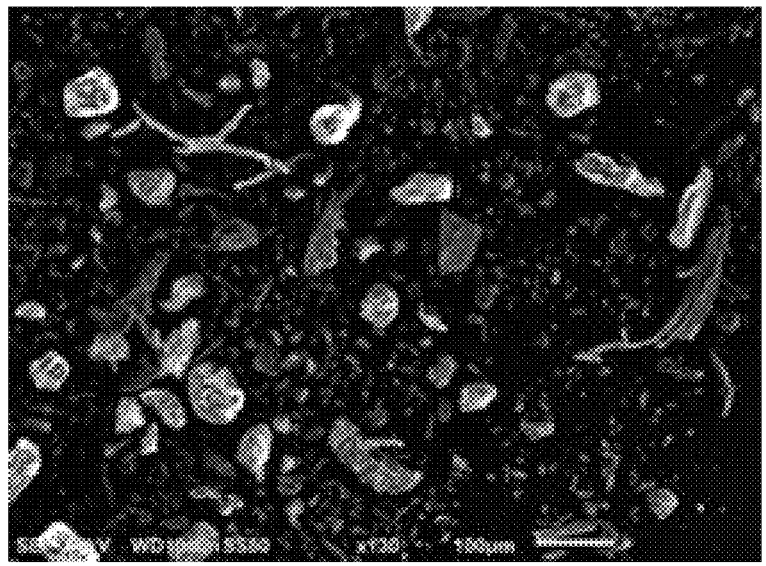
FIG. 2 shows an electron micrograph of rice husk before milling

As shown in Example 1, rice husk did not function effectively as a flow agent for a poor-flowing spray dried powder. It was hypothesized that the rice husk did not function effectively because of its large particle size as compared to silicon dioxide that it typically used as a flow agent for powders comprising flavors and fragrances. Ball milling was used to reduce the size of the rice husk. The ball milling was carried out in two stages. The first stage ball milling parameters are provided below:
1) Stainless Steel mill jar with 1230 cc capacity;
2) Rotation speed of mill jar: 210 RPM;
3) Stainless Steel Bead (W.W. Grainger Inc.): 25.4 mm (2 balls), 9.5 mm (151 balls), & 6.4 (99 balls) mm with total volume of mixed ball set of about 100 cc;
4) Volume ratio of Nu-Flow® powder to stainless steel beads: 50:50;
5) First stage ball milling time: 72 hours Ball milling significantly reduced the particle size and size; distribution of Nu-Flow® (see Table 2, FIGS. 2 and 3, 5).

After first stage ball milling for 72 hours, the particle sized of the rice husk was measured. After ball milling for 72 hours, 77.9% of particles were shown to be less than 10 µm and 90% by weight of particles were shown to be less than 14.8 µm. The size reduced rice husk was evaluated as a flow agent. Ball milled Nu-Flow® was added to the Control at different levels ranging from 0 to 2% by weight of the powders. The resultant powder mixture was blended manually until uniformly mixed. Sample was taken for analysis of flow properties. We found that particle size reduction of Nu-Flow® rice husk greatly improved its functionality as a flow agent. When 2% ball milled Nu-Flow® was added to the Orange Spray Dry Powder, the avalanche energy was decreased from 1484 to 678 Pascal/kg. When 2% Nu-Flow® as is was added, the avalanche energy was 1453 Pascal/kg. This clearly demonstrates that particle size and particle size distribution of $^{NuFlow}$® are critical in order to function effectively as a flow agent.

The sample collected after first stage ball milling was subjected to a second stage ball milling using the same device but with smaller balls (3100 stainless steel balls with 4 mm diameter). The $2^{nd}$ stage ball milling further reduced the particle size and size distribution of the Nu-Flow® rice husk (see Table 2, FIGS. 2 and 4, 5). After 144 hours of $2^{nd}$ stage milling, 89.0% by weight of particles are less than 10 µm and 90% by weight of particles are less than 10.2 µm.

The Nu-Flow® after $2^{nd}$ stage ball milling was evaluated as a flow agent. Balled milled Nu-Flow® was added to the Control at different levels ranging from 0 to 1% by weight. The resultant powder mixture was blended manually until uniformly mixed. Samples were taken for analysis of flow properties. When 0.75%, $2^{nd}$ stage ball milled Nu-Flow® rice husk was added to the Control, the avalanche energy decreased from 1484 to 825 Pascal/kg (see FIG. 6). When 2% Nu-Flow® rice husk was added without milling, the avalanche energy was 1453 Pascal/kg. This confirmed that Nu-Flow® could be an effective flow agent after size reduction.

TABLE 2

Particle size distribution of Nu-Flow ® before and after ball milling

| Nu-Flow ® | Particle fraction of <10 µm | Mean particle size, $d_{43}$* (µm) | Median particle size $d_{50}$** (µm) | $d_{75}$** (µm) | $d_{90}$** (µm) |
|---|---|---|---|---|---|
| Before milling | 20.4% | 50.6 | 39.9 | 69.4 | 109.5 |
| $1^{st}$ stage milling for 72 hours | 77.9% | 7.1 | 4.7 | 9.5 | 14.8 |
| $2^{nd}$ stage milling for 144 hours | 89.0% | 4.8 | 3.2 | 6.2 | 10.2 |

*$d_{43}$, volume mean diameter;
**$d_{50}$, $d_{75}$, $d_{90}$ defines the upper size range of 50%, 75%, and 90% by weight of particles, respectively.

What is claimed is:
1. Rice husk particles wherein at least 90%, by weight, of the total weight of the particles, has a diameter less than 25 µm, and wherein the particles have a volume mean diameter of about 8 µm to about 22 µm.

2. The rice husk particles as recited in claim 1 wherein at least 75%, by weight, of the total weight of the particles, has a diameter less than 15 μm.

3. The rice husk particles as recited in claim 2 wherein at least 50%, by weight, of the total weight of the particles, has a diameter less than 10 μm.

4. Rice husk particles wherein at least 50%, by weight, of the total weight of the particles, has a diameter less than 10 μm, and at least 75%, by weight, of the total weight of the particles, has a diameter less than 15 μm, and at least 90%, by weight, of the total weight of the particles has a diameter less than 25 μm, and wherein the particles have a volume mean diameter of about 8 μm to about 22 μm.

5. The rice husk particles as recited in claim 4 wherein at least 50%, by weight, of the total weight of the particles, has a diameter less than 5 μm, and at least 75%, by weight, of the total weight of the particles, has a diameter less than 10 μm, and at least 90%, by weight, of the total weight of the particles has a diameter less than 15 μm.

6. Rice husk particles wherein at least 70%, by weight, of the total weight of the particles, have a volume mean diameter of about 8 μm to about 12 μm.

7. The rice husk particles of claim 6 wherein the particles have a volume mean diameter of about 10 μm.

8. Rice husk particles wherein at least 90%, by weight, of the total weight of the particles, have a volume mean diameter about 8 μm to about 22 μm.

9. The rice husk particles of claim 8 wherein the particles have a volume mean diameter of about 20 μm.

10. A spray dried powder comprising a flavor or fragrance, a carrier and rice husk particles, wherein the rice particles are present in an amount up to about 5% by weight, and wherein the powder has flowability of about no more than 1,000 Pascal/kg.

* * * * *